United States Patent [19]
Vardiman et al.

[11] Patent Number: 6,021,678
[45] Date of Patent: Feb. 8, 2000

[54] APPARATUS FOR TRANSPORTING EMISSIONS FROM A STACK

[75] Inventors: Steven Vardiman, Sandy, Utah; Andrew R. McFarland, College Station, Tex.

[73] Assignees: Kennecott Utah Copper Corporation, Magna, Utah; The Texas A&M University System, College Station, Tex.

[21] Appl. No.: 09/085,649

[22] Filed: May 27, 1998

[51] Int. Cl.⁷ .................................................. G01N 1/00
[52] U.S. Cl. .................................. 73/863.11; 73/863.23; 73/866.5
[58] Field of Search ................................ 73/863, 863.01, 73/863.11, 866.5, 23.31, 863.23, 23.33

[56] References Cited

U.S. PATENT DOCUMENTS

| | | | |
|---|---|---|---|
| 3,665,199 | 5/1972 | Cahill et al. | 250/106 S |
| 3,766,971 | 10/1973 | Baum | 165/1 |
| 3,784,902 | 1/1974 | Huber | 73/421.5 |
| 3,793,887 | 2/1974 | Anderson et al. | 73/421.5 R |
| 3,794,909 | 2/1974 | Smith | 324/32 |
| 3,841,145 | 10/1974 | Boubel | 73/28 |
| 3,889,121 | 6/1975 | Bossen | 250/379 |
| 3,965,748 | 6/1976 | Boubel et al. | 73/421.5 A |
| 3,983,743 | 10/1976 | Olin et al. | 73/28 |
| 4,017,186 | 4/1977 | Shofner et al. | 356/103 |
| 4,141,238 | 2/1979 | Steen | 73/28 |
| 4,161,883 | 7/1979 | Laird et al. | 73/421.5 |
| 4,686,848 | 8/1987 | Casselberry et al. | 73/38 |
| 5,058,440 | 10/1991 | Graze, Jr. | 73/863.83 |
| 5,279,970 | 1/1994 | Patashnick et al. | 436/133 |
| 5,332,512 | 7/1994 | Wells | 210/790 |
| 5,349,844 | 9/1994 | Lilienfeld | 73/28.01 |
| 5,369,981 | 12/1994 | Merz et al. | 73/28.01 |
| 5,415,025 | 5/1995 | Bartman et al. | 73/23.2 |
| 5,490,429 | 2/1996 | Jarolics | 73/863.83 |
| 5,526,685 | 6/1996 | Davis | 73/262 |
| 5,571,945 | 11/1996 | Koutrakis et al. | 73/28.03 |
| 5,759,482 | 6/1998 | Gregory et al. | 266/79 |

OTHER PUBLICATIONS

Ranade, Madhav B., Werle, Donald K., and Wasan, Darsh T., "Aerosol Transport Through a Porous Sampling Probe With Transporation Airflow", Jul. 1976, pp. 42–52 *Journal of Colloid and Interface Science*, vol. 56, No. 1.

Giever, Paul M., "Automatic Instrumentation in Industrial Hygiene" 1974, pp. 1–5 *Advances in Instrumentation*, Paper 738.

*Primary Examiner*—Hezron Williams
*Assistant Examiner*—Thuy Vinh Tran
*Attorney, Agent, or Firm*—Whyte Hirschboeck Dudek SC

[57] ABSTRACT

The apparatus and method of the present invention extract samples of emissions within a stack or duct through the use of a probe. The sample is transported from the probe through a transport device into a mass-monitoring device in which the amount of particulate matter contained in the sample of the emissions is continuously analyzed. The apparatus of the present invention includes a transport device which has a porous inner tube completely sealed inside a solid outer tube. The outer tube of the transport device is supplied with gas through a transpiration port in the outer tube. The gas permeates from the outer tube through the porous inner tube in order to reduce deposition by keeping the particulate matter suspended within the porous inner tube. The method of the present invention continuously analyzes the amount of particulate contained within a sample of the emissions collected from a stack or duct by (i) extracting a sample of particular matter from a stack or duct by using a probe, (ii) transporting the sample of the emissions from the probe through the aforementioned transport device into a mass-monitoring device, while simultaneously supplying a gas into the outside tube of the transport device such that gas flows from the outer tube through the porous inner tube to reduce deposition of particulate matter onto the porous inner tube, and (iii) continuously analyzing the amount of particulate contained in the emissions received from the transport device. Problems associated with deposition of the particulate matter contained within the sample of the emissions after collection by the probe and prior to analysis are reduced with the present invention resulting in greater accuracy when monitoring the amount of particulate matter emitted from a stack.

20 Claims, 5 Drawing Sheets

APPARATUS FOR TRANSPORTING EMISSIONS FROM A STACK

BACKGROUND OF THE INVENTION

The present invention relates to an apparatus and method for continuously monitoring the amount of particulate contained in emissions which are sampled from a smoke stack and measured at a location outside of the stack.

Emissions from smoke stacks are monitored in order to determine the nature and quantity of the matter which is emitted into the atmosphere. Such emissions have been, and will most likely continue to be, the subject of significant government regulation. At present, particulate mass is the only regulated variable of stack emissions for which there is no true real-time measurement.

Emissions are sampled from the stack using a variety of well known devices, including probes, nozzles, and tubes which perform sampling according to standards established by the United States Environmental Protection Agency and the American National Standards Institute.

Once extracted from the stack flow, the emissions, which include particulate, are transported outside of the stack to a measuring device which determines the amount of particulate matter contained within the emissions. The transport pipe used to carry the emissions is important because during transport of the sample from the stack to the measuring device for analysis, there is deposition of the particulate contained with the emissions to the transport pipe as the result of gravitational, thermal diffusion, and turbulent losses. These depositional losses prevent the particulate matter from being analyzed by the measuring device leading to incomplete measurement of the amount of particulate contained within the emissions. The rate of gravitational, diffusional and turbulent deposition losses depends on such factors as the flow rate of the emissions through the pipe, particle size and the pipe geometry.

Complex calculations are required in order to predict the depositional losses of particulate matter. Software can be used to provide estimates on the amount of particle transmission and/or deposition for a range of particle diameters; however, on a real-time basis it is generally not possible to correct the amount of particulate matter transmitted through the system to take into account the losses. Any attempt to make such a correction leads to uncertainty in sampling results.

There is a variety of conventional devices that are used to estimate the mass of particulate matter in emissions which are expelled from a smoke stack.

One well-known apparatus is a light attenuation system that is based on the extinction of a light beam as it traverses the stack. Though this apparatus provides monitoring on a real-time basis, true mass correlation with light attenuation is not possible which can lead to inaccurate results.

A second apparatus involves obtaining actual mass data by a batch sampling technique with a retrospective analysis. In this apparatus, a probe is inserted into a stack at a number of different locations in order to extract a composite sample of the particulate matter. This sample is analyzed at a later time in order to determine the average of the mass of particulate emitted from the stack. The procedure involves washing the inside of the probe and transport line to recover wall losses. This batch sampling, which can provide accurate values of mass concentration, is not capable of real-time measurement of the particulate mass within emissions.

While conventional systems can either provide real-time data or mass emission data, they cannot provide both. For the foregoing reasons a need exists for an apparatus and method for extracting representative samples from a stack, and transporting the sample to a mass-monitoring device in order to continuously analyze the amount of particulate contained within the emissions without significant loss of particulate matter due to deposition.

SUMMARY OF THE INVENTION

The present invention provides an apparatus and method for continuously monitoring the amount of particulate matter contained within emissions from a smoke stack. The apparatus and method both provide for the transfer of emissions from a smoke stack to a mass-monitoring device with minimal loss of particulate due to deposition. Minimizing particulate deposition is important in order to accurately and continuously measure the amount of particulate contained within the emissions.

The apparatus of the present invention includes (i) a probe for extracting a sample of the emissions from within the smoke stack, (ii) a transport device for transporting the emissions from the probe to a mass-monitoring device located outside the stack, and (iii) the mass-monitoring device.

The transport device within the apparatus includes a porous inner tube having an inlet that is placed in open communication with the probe and an outlet that is placed in open communication with the mass-monitoring device or with a flow splitter placed between the porous inner tube and the mass monitoring device. The transport device further includes an outer tube which completely surrounds the porous inner tube and is sealed to the porous inner tube by a sealing means. The sealing means ensures that a gas, which is supplied into the outer tube, flows from the interior of the outer tube through and into the porous inner tube. The gas is supplied into the outer tube through one or more ports. The flow of gas from the outer tube into the porous inner tube minimizes particulate matter contact with, and deposition on, the internal wall of the porous inner tube. Using the transport device to minimize particulate deposition during transport of the emissions improves the accuracy of the results obtained from continuously monitoring the amount of particulate contained within emissions.

The transport device may also include at least one support for the porous inner tube which bears against the outer tube to provide reinforcement to the porous inner tube. The support design does not significantly restrict the flow of gas throughout the entire length of the outer tube so that gas flows about, and then permeates through, the entire length of the porous inner tube in order to prevent the particulate matter contained within the emissions from depositing on the porous inner tube.

The apparatus may also include a thermal control device for maintaining the temperature of the gas supplied through the port in the outer tube to a level above the dew point temperature of the emissions collected from the smoke stack in order to prevent condensation on the internal wall of the porous inner tube.

The apparatus may further include temperature sensors attached to the probe in order to determine the temperature of the emissions entering the probe. Knowing the temperature of the emissions establishes the minimum level for the temperature of the gas which flows from the outer tube through the porous inner tube.

The apparatus may also include a velocity sensor (e.g., an S-type pitot tube) attached in the vicinity of the probe in order to determine the free-stream velocity of the emissions entering the probe.

The present invention also includes a method for continuously analyzing the amount of particulate matter in smoke stack emissions. The method comprises the steps of (i) extracting a sample of the emissions from a smoke stack using a probe, (ii) transporting the sample from the probe through the porous inner tube of the aforementioned transport device into a mass-monitoring device located outside the stack, while simultaneously supplying a gas into the outer tube of the transport device such that the gas permeates from the outer tube through the porous inner tube of the transport device, and (iii) continuously analyzing the amount of particulate contained in the emissions received from the transport device through use of a mass-monitoring device.

DETAILED DESCRIPTION OF INVENTION

Similar reference characters denote corresponding features consistently through the attached drawings. Various items of equipment such as fasteners, fittings, etc., are omitted so as to simplify the description. However, those skilled in the art will realize that such conventional equipment can be employed as desired.

Figure 1:
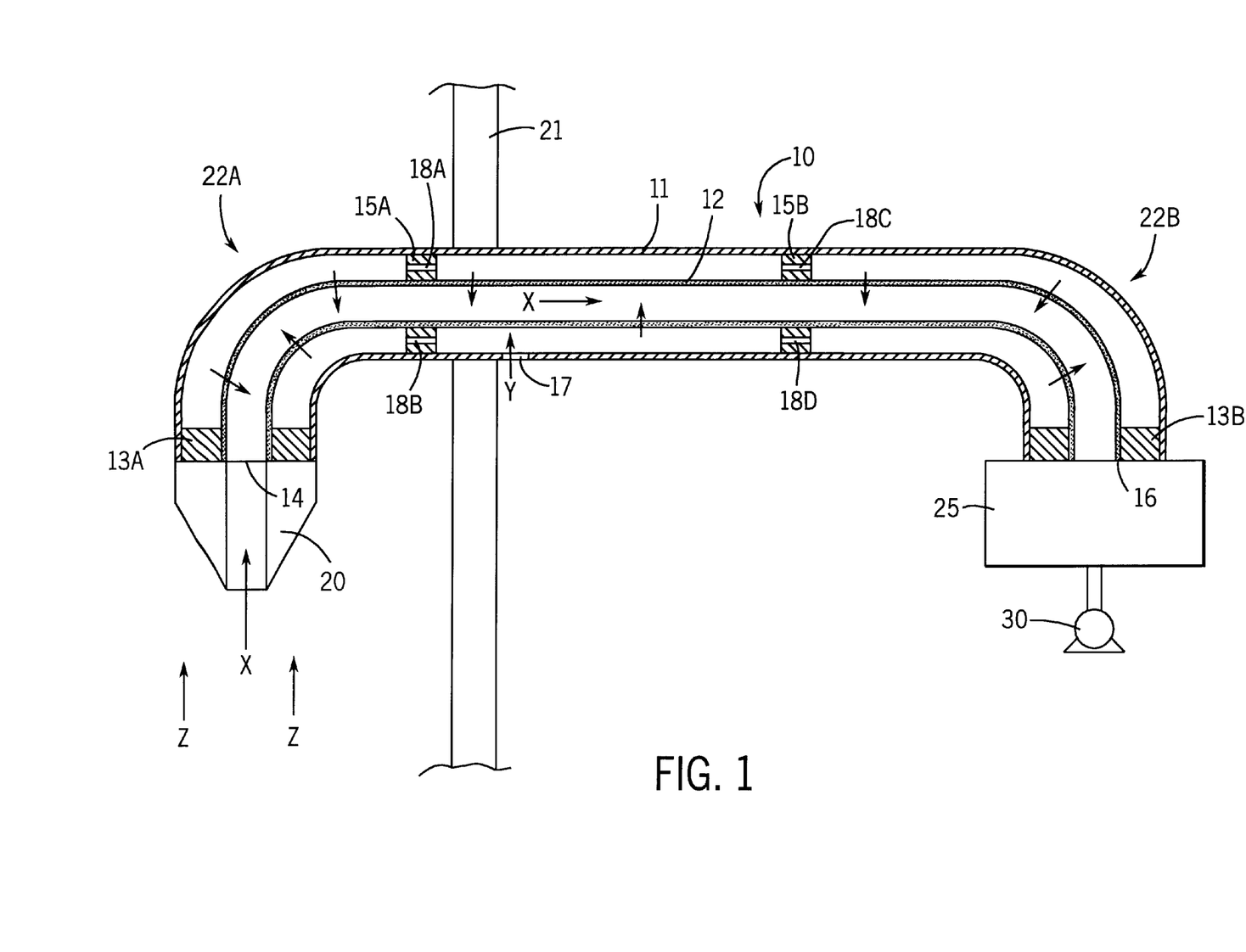
FIG. 1 is a partial section view of an apparatus of the present invention for continuously monitoring the amount of particulate contained in a continuously flowing sample of the emissions from a smoke stack.

As shown in FIG. 1, the apparatus of the present invention includes probe 20 which collects a sample X of the emissions from a location within smoke stack 21 where the particulate mass concentration at the said location is representative of the average mass concentration across the stack cross sectional area. A sample of the emissions Z, including any particulate matter contained therein, flows from probe 20 through inlet 14 into porous inner tube 12 and then from porous inner tube 12 through outlet 16 into mass-monitoring device 25. By using transport device 10 to transfer the sample X from probe 20 to mass-monitoring device 25, the amount of particulate matter, which is lost due to deposition before the sample X can be analyzed, is reduced. This reduction in deposition of the particulate matter leads to increased accuracy when continuously monitoring the amount of particulate contained within the sample X.

Figure 2:
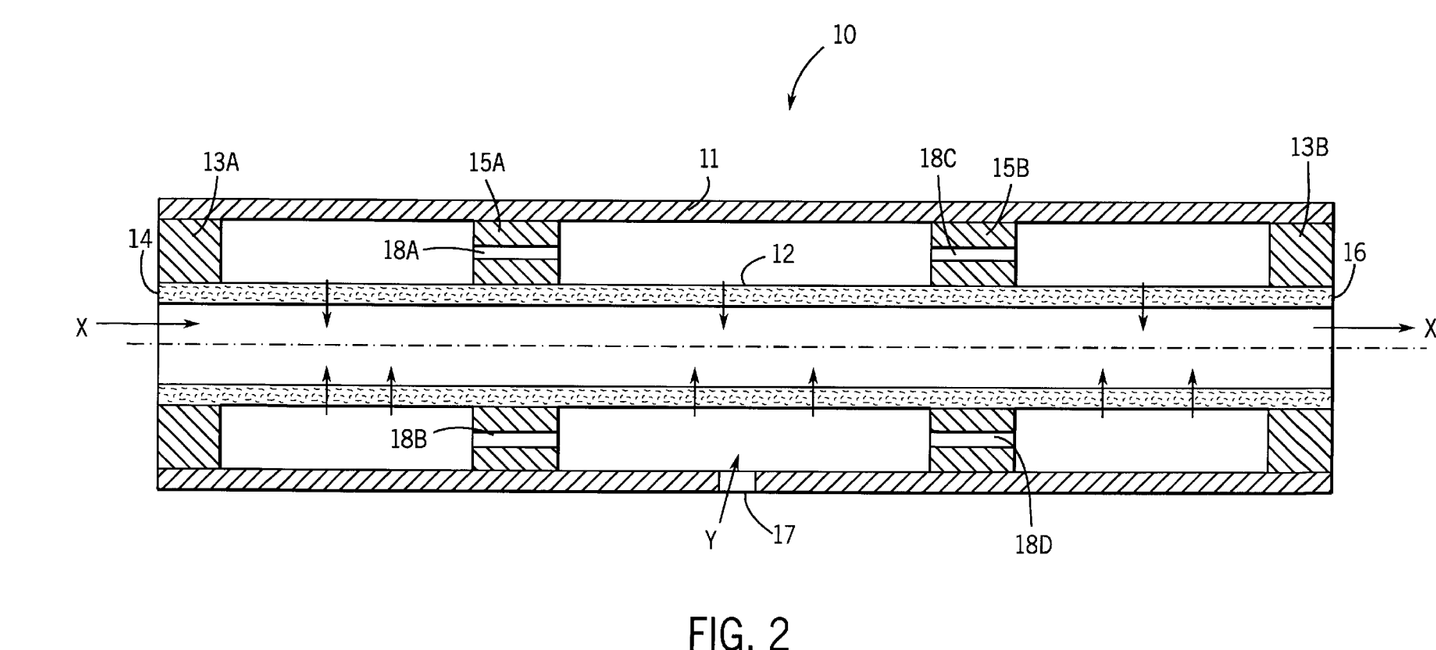
FIG. 2 is a section view of a transport device which may be used in the apparatus of the present invention for transporting emissions extracted from a smoke stack to a mass-monitoring device.

FIG. 2 shows one embodiment of transport device 10. Transport device 10 includes solid, nonporous outer tube 11 which is sealed about porous inner tube 12, preferably using seals 13A, 13B. Seals 13A, 13B are preferably configured using flanges and O-rings to maintain a dust tight seal between porous inner tube 12 and outer tube 11. A preferred design configuration allows apparatus 10 to be disassembled for cleaning and maintenance among other reasons. Porous inner tube 12 and outer tube 11 may also be welded together, or be part of an integrally molded unit. In addition, porous inner tube 12 and outer tube 11 may be fabricated such that they are crimped or otherwise joined during assembly to form a seal.

Figure 4:
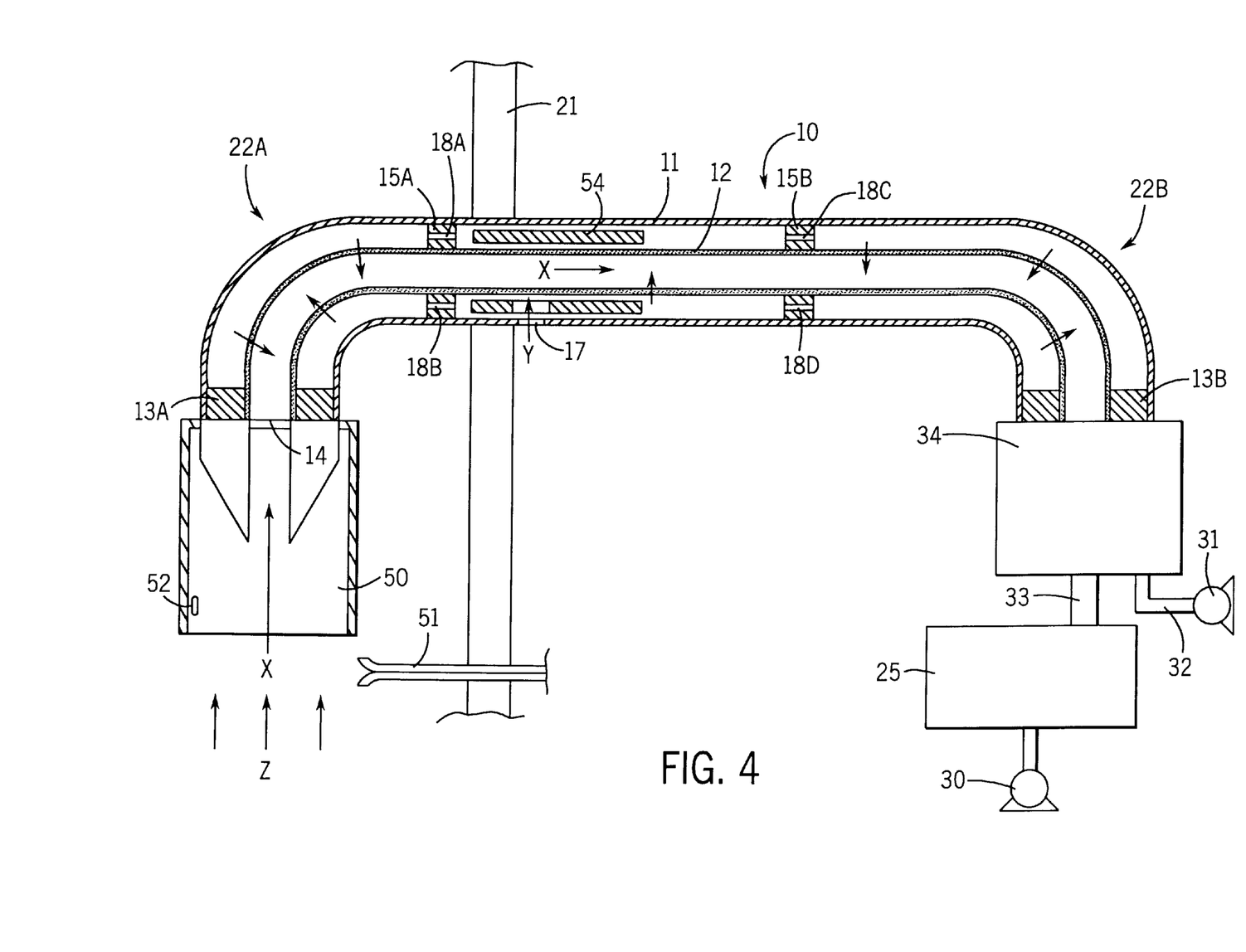
FIG. 4 is a partial section view of another embodiment of the apparatus of the present invention.
Figure 5:
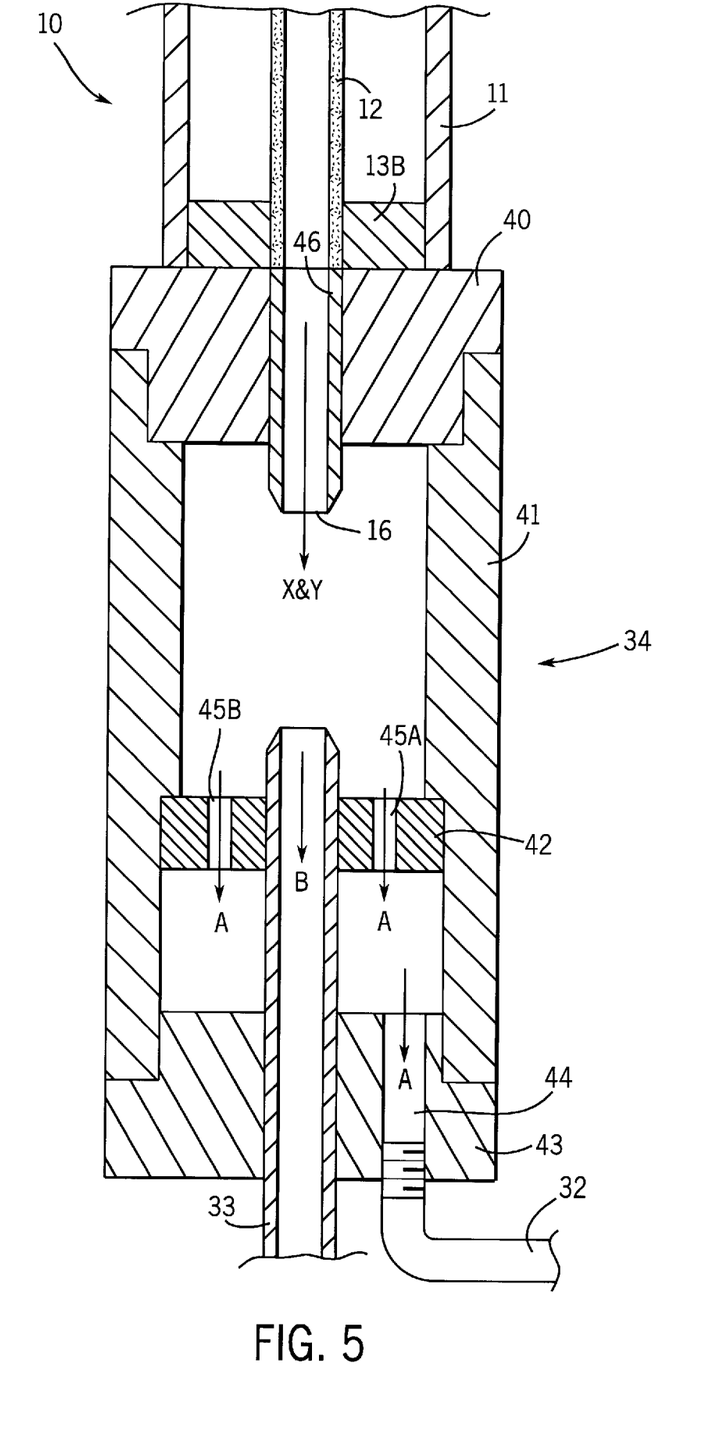
FIG. 5 is a section view of the splitter used in the apparatus of FIG. 4.

The length and shape of transport device 10 may vary depending on the size of the stack and physical arrangement of the location where the mass-monitoring device is located. Transport device 10 may have one or more bends 22A, 22B (as shown in FIGS. 1 and 4), which may be required to change the direction of the sample stream as it passes from the probe 20 to the outlet 16. Bends 22A, 22B preferably have a radius of curvature that is at least two, and even more preferably three, times the outside diameter of porous inner tube 12. Porous inner tube 12 and outer tube 11 may have circular, oval, square and rectangular cross sections among others, and each may be different from the other, e.g. the porous inner tube can have a circular cross-sectional area while the nonporous outer tube has a polygonal cross-sectional area. The material and relative diameters of porous inner tube 12 and outer tube 11 as well as the size of the pores in porous inner tube 12 will vary depending such design factors as the flow rate and temperature of the sample X as well as the average size of the particulate matter contained with the the sample. Porous inner tube 12 is typically made of stainless steel and has pores which are between about 0.2–0.8 $\mu$m, and preferably about 0.4–0.6 $\mu$m. Outer tube 11 is preferably a high nickel alloy which is typically used in high temperature, corrosive environments. A typical high nickel alloy tube is manufactured by Haynes-Stellite Company and is sold under the trademark HASTALLOY.

Gas Y is supplied into outer tube 11 through port 17. Port 17 is preferably located near the center of the axial length of outer tube 11, and additional transpiration ports may be placed in outer tube 11 in order to more evenly distribute the flow of gas Y to porous inner tube 12.

Seals 13A, 13B ensure that gas Y flows through porous inner tube 12 minimizing contact between any particulate matter contained in sample X and porous inner tube 12 reducing the amount of deposition of particulate onto the inner wall of porous inner tube 12. Gas Y is preferably dry filtered air, but may be recirculated stack emissions from which the particulate matter has been removed.

Gas Y is preferably under sufficient pressure to ensure that the velocity of gas Y, when flowing through porous inner tube 12, is greater than the deposition velocity of a selected size of the particulate matter which is directed toward the inside of porous inner tube 12 in order to force the particulate matter to remain suspended within porous inner tube 12. Typically the selected particle size is 10 $\mu$m aerodynamic diameter, AD, although other sizes may be selected as well. The particle deposition velocity includes the effects of both sedimentation and turbulent diffusion. The flow of gas Y through porous inner tube 12 tends to create a buffer zone between sample X and porous inner tube 12, which reduces the probability that aerosol particles of not only the selected size, but of other sizes as well, will contact the wall of the porous inner tube 12. Another factor leading to reduced sedimentation losses of particulate matter is the addition of gas Y to sample stream X which causes the gas velocity inside the porous inner tube 12 to increase as the sample stream flows from inlet 14 to exit 16. The increased velocity of sample X within transport device 10 leads to shorter residence time of sample X within transport device 10. Because the particulate matter contained in sample X spends less time within transport device 10, the potential for losses by gravitational setting of the particulate matter to porous inner wall 12 is reduced.

Transport device 10 may further include at least one structural support which reinforces porous inner tube 12 by bearing against outer tube 11 to ensure that porous inner tube 12 is properly aligned within outer tube 11. In a preferred embodiment, supports 15A, 15B provide support to porous inner tube 12 and have openings 18A, 18B, 18C, 18D which permit gas Y to flow from transpiration port 17 throughout the entire length of outer tube 11.

Figure 3:
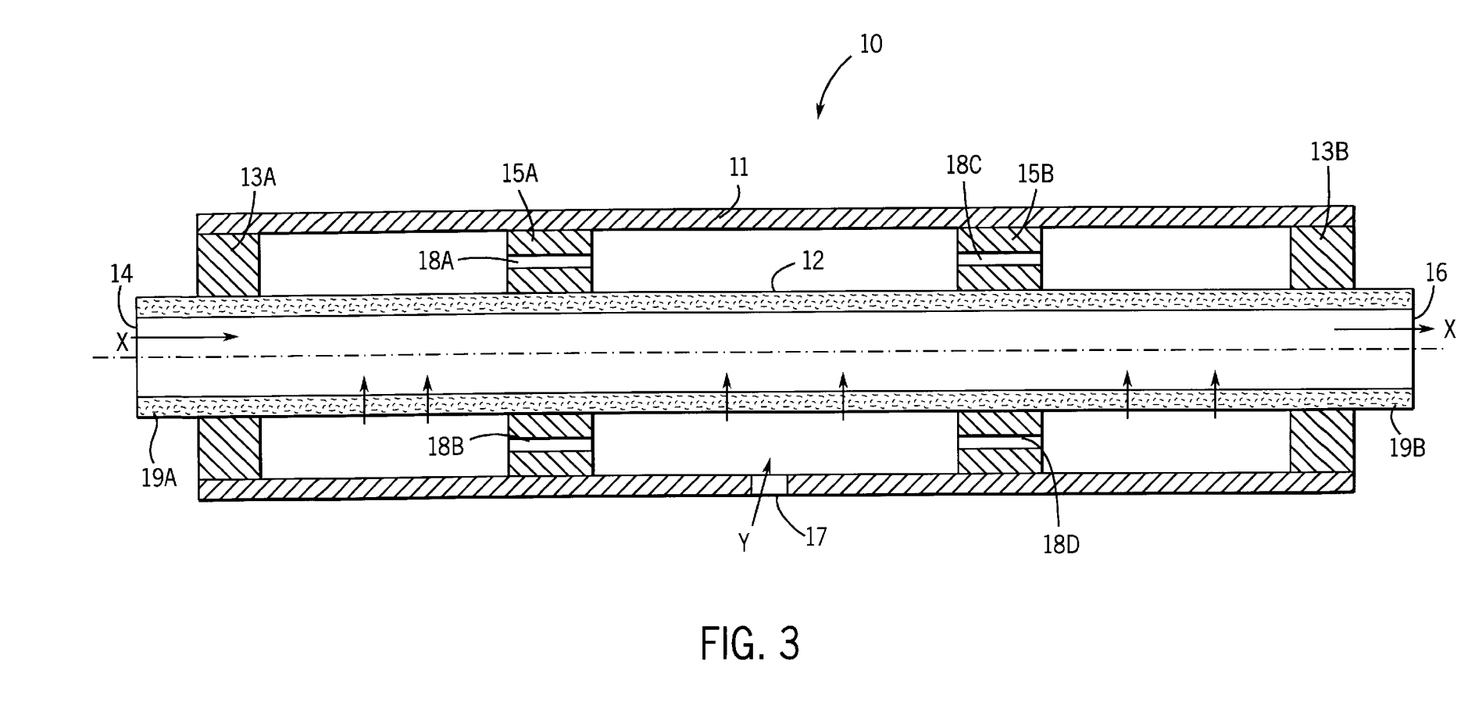
FIG. 3 is a section view of another transport device which can be used in the apparatus of the present invention.

Another embodiment of transport device 10 is shown in FIG. 3. Ends 19A, 19B of porous inner tube 12 may protrude between seals 13A, 13B from outer tube 11 and extend into a bend, a probe, a flow splitter, or a mass-monitoring device in order to facilitate mating transport device 10 with these devices depending on their design.

Mass-monitoring device 25 is preferably a beta attenuation monitor which extracts particulate from emissions X and gas Y on a filter strip. The mass of the particulate matter deposited on an area on the filter strip is measured continuously to provide a real time measurement of the amount of particulate contained within sample X. The beta attenuation monitor draws in either a representative portion of sample X and gas Y, or all of the sample X and gas Y with the aid of pump 30. A preferred beta attenuation monitor is GRASEBY-ANDERSEN PM-10 Beta Gauge Automated Dust Measuring Instrument Model No. FH62 I-N, which is distributed by Graseby Andersen Incorporated of Smyrna, Ga.

A sample of emissions Z is preferably collected using a single probe 20 from one location within a stack 21, or a duct (not shown). The opening of probe 20 where sample X enters is preferably axially aligned with the flow of emissions Z within the smoke stack 21. Modifications based on such considerations as the velocity of gas containing emissions Z, the flow rate of sample X and the anticipated aerosol particle size can be made to the design of probe 20 to facilitate the transmission of particulate matter through probe 20.

Referring now to FIG. 4, a shrouded probe 50 is preferably used in the apparatus of the present invention. A shroud placed about the probe decelerates the flow of emissions Z which results in lower deposition of particulate matter within the probe. Use of shrouded probe 50 results in approximately constant transmission of aerosol in sample X even when the velocity of emissions Z within stack 21 varies. A preferred shrouded probe which may be used for sampling is disclosed in U.S. Pat. No. 4,942,774, which is incorporated herein by reference, and is manufactured by Graseby Andersen, Incorporated of Smyrna, Ga.

S-type pitot tube 51 may also be incorporated into the apparatus of the present invention to determine the free-stream velocity of emissions Z in the region of smoke stack 21 where shrouded probe 50 is collecting sample X. The design of S-type pitot tube 51, and the location of S-type pitot tube 51 within smoke stack 21 relative to shrouded probe 50, is specified in Appendix A of 40 CFR § 60 (1995).

Temperature sensor 52 may be attached to shrouded probe 50 to monitor the temperature of sample X entering the apparatus. The temperature of sample X should be determined so that the temperature of gas Y which is supplied to outer tube 12 can be maintained at a level equal to, or above, the temperature of sample X to prevent vapor condensation onto porous inner tube 12.

Gas Y delivered through transpiration port 17 may be heated to prevent condensation of sample X onto porous inner tube 12, especially when analyzing emissions with high dew point temperatures. A thermal control apparatus is preferably used to heat gas Y to a temperature equal to, or greater than, sample X collected from the smoke stack. The thermal control apparatus is typically a heating apparatus which is preferably located either in close proximity to outer tube 12 near transpiration port 17, or even more preferably cartridge heater 54 placed in the annular region between porous inner tube 12 and outer tube 11 of transport device 10.

The present invention may also comprise splitter 34 because of the limited air handling capacity of mass-monitoring device 25. As stated previously, mass-monitoring device 25 is preferably a beta attenuation monitor, and beta attenuation monitors typically have limited air handling capacity. Splitter 34 is therefore used to reduce the amount of sample X and gas Y which enters the beta attenuation monitor, or some other mass-monitoring device.

A sampling portion consisting of sample X and gas Y is drawn from splitter 34 by pump 30 through primary outlet 33 into mass-monitoring device 25 for analysis, while the remaining portion also consisting of sample X and gas Y is drawn from splitter 34 by pump 31 into secondary outlet 32.

A preferred embodiment of splitter 34 is shown in more detail in FIG. 5. A non-porous extension tube 46 of porous inner tube 12 extends into splitter 34 and is secured within inlet hub 40 such that sample X and gas Y flow from outlet 16 into drift tube 41. As sample X and gas Y flow through drift tube 41 the flow is divided into sampling portion B which is drawn through primary outlet 33 into mass-monitoring device 25, and remaining portion A, which is drawn through one or more openings 45A, 45B in manifold 42, and then through opening 44 in outlet hub 43 before entering secondary outlet 32. Remaining portion A is then either discharged, or filtered and recirculated for use as gas Y to be feed into outer tube 11 of transport device 10. Length of drift tube 41 is selected so that sampling portion B is representative of the mixture of sample X and gas flow Y.

Porous inner tube 12, inlet hub 40, drift tube 41, manifold 42, outlet hub 43, primary outlet 33 and secondary outlet 32 may be joined together in a variety of air-tight design configurations, including but not limited to, welding, molding and press fitting, and may be further secured through the use of seals, gaskets and/or O-rings.

The relative percentage of sample X and gas Y which divide into sampling portion B and remaining portion A are defined by the magnitude of the cross-sectional area of the interior opening of primary outlet 33 relative to the magnitude of the cross-sectional area of the interior opening of drift tube 41. Sampling portion B is representative of the mixture of sample X and gas flow Y. Splitter 34 is preferably designed such that the flow rate of sampling portion B from splitter 34 is no greater than the maximum air handling capacity of mass-monitoring device 25.

The present invention also includes a method for continuously analyzing the amount of particulate contained within sample X or emissions Z collected from smoke stack 21. First, sample X is extracted from emissions Z by probe 20. Second, sample X is transported from probe 20 through transport device 10 into mass-monitoring device 25, while simultaneously supplying gas Y through transpiration port 17 into outer tube 11 of transport device 10 such that gas Y permeates from inside outer tube 11 into porous inner tube 12. Finally, sample X of emissions Z is continuously analyzed in mass-monitoring device 25 in order to estimate the amount of particulate matter contained within emissions Z.

Although the present invention has been described in considerable detail with reference to certain preferred versions thereof, other versions are possible. The transport device may contain various designs for the porous inner tube, outer tube and transpiration port, including various sizes, shapes and materials. In addition, the present invention may use a variety of conventional probes, heaters, splitters and mass-monitoring devices.

What is claimed is:

1. An apparatus for continuously monitoring the amount of particulate contained in a sample of emissions extracted from a smokestack, the apparatus comprising:
   a) a probe for collecting the emissions having particulate matter from within the smoke stack, and
   b) a transport device for transporting the emissions and particulate matter collected from the probe comprising;
      a porous inner tube having an inlet and an outlet, the inlet in open communication with the probe such that the emissions and particulate matter flow from the probe into the porous inner tube,
      an outer tube completely enclosing the inner tube, the outer tube comprising a transpiration port for feeding a gas into the outer tube to reduce deposition of the emissions and particulate matter in the porous inner tube, and
      means for sealing the outer tube to the porous inner tube.

2. The apparatus of claim 1 in which the transport device further comprises at least one support for the porous inner tube that provides stability to the porous inner tube by bearing against the outer tube without blocking the gas flow through the outer tube.

3. The apparatus of claim 1 further comprising a S-type pitot tube attached to the probe for measuring free-stream velocity of the emissions collected by the probe.

4. The apparatus of claim 1 further comprising at least one temperature sensor attached to the probe for measuring temperature of the emissions extracted by the probe.

5. The apparatus of claim 4 further comprising a temperature control system for maintaining the temperature of a gas inserted into the outer tube at a level at least as high as a dew point temperature of the emissions entering the probe.

6. The apparatus of claim 5 in which the temperature control system is a cartridge heater located between the outer tube and the porous inner tube of the transport device.

7. The apparatus of claim 10 in which the mass monitoring device is a beta attenuation monitor.

8. The apparatus of claim 1 in which the probe is a shrouded probe.

9. The apparatus of claim 1 in which the inner and outer tubes are in concentric axial alignment.

10. The apparatus of claim 1 further comprising a mass-monitoring device in open communication with the outlet of the porous inner tube.

11. An apparatus for continuously monitoring the amount of particulate contained in a sample of emissions extracted from a stack, the apparatus comprising:
    a) a probe for collecting the emissions from within the stack;
    b) a transport device for transporting the emissions collected from the probe comprising:
       a porous inner tube having an inlet and an outlet, the inlet in open communication with the probe such that emissions flow from the probe into the porous inner tube,
       an outer tube completely enclosing the inner tube, the outer tube comprising a transpiration port for feeding a gas into the outer tube, and
       means for sealing the outer tube to the porous inner tube; and
    c) a mass-monitoring device in open communication with the outlet of the porous inner tube, wherein the inlet and the outlet of the porous inner tube are not enclosed within the outer tube, the inlet being sealed within the probe and the outlet being sealed within the mass-monitoring device.

12. A method for continuously analyzing concentration of particulate matter content in emissions from stacks or ducts, the method comprising the steps of:
    a) extracting a sample of the emissions from a stack or duct using a probe,
    b) transporting the sample of the emissions extracted by the probe through a porous inner tube of a transport device into a mass-monitoring device while simultaneously supplying a gas through a transpiration port into an outside tube of the transport device such that the gas permeates from the outside tube through the porous inner tube to reduce deposition of the particulate matter contained in the sample and the porous inner tube, and
    c) analyzing the mass of the particulate matter received from the transport device in a mass-monitoring device.

13. The method of claim 12 in which the gas supplied through the transpiration port is heated to prevent the sample from condensing on the porous inner tube.

14. The method of claim 13 in which the gas supplied through the transpiration port is under sufficient pressure to keep the velocity of the gas permeating through the porous inner tube greater than a deposition velocity of a selected particulate size directed toward the porous inner tube.

15. An apparatus for continuously monitoring the amount of particulate matter contained in emissions collected from a smoke stack, the apparatus comprising:
    a) a probe for extracting a sample of the emissions from within the smoke stack,
    b) a transport device for transporting the emissions collected from the probe comprising;
       a porous inner tube having an inlet and an outlet, the inlet in open communication with the probe such the sample of the emissions flows from the probe into the porous inner tube,
       an outer tube completely enclosing the porous inner tube, the outer tube comprising a transpiration port for feeding a gas into the outer tube,
       means for sealing the outer tube to the porous inner tube,
    c) a splitter in open communication with the outlet of the porous inner tube for receiving the sample of the emissions and the gas from the transport device such that a sampling portion of the emissions and the gas flow through a primary outlet and a remaining portion of the sample of the emissions and the gas flow through a secondary outlet of the splitter, and
    d) a mass-monitoring device in open communication with the primary outlet of the splitter adapted to receive the emissions and gas from the primary outlet of the splitter for continuously analyzing the particulate contained within the emissions.

16. The apparatus of claim 15 in which the transport device further comprises at least one support for the porous inner tube that provides stability to the porous inner tube by bearing against the outer tube without blocking the gas flow through the outer tube.

17. The apparatus of claim 15 further comprising a temperature control system for maintaining a temperature of the gas inserted into the outer tube at a level at least as high as a dew point of the emissions entering the probe.

18. The apparatus of claim 17 in which the temperature control system is a cartridge heater located between the outer tube and the porous inner tube of the transport device.

19. The apparatus of claim 15 in which the mass monitoring device is a beta attenuation monitor.

20. The apparatus of claim 15 in which the splitter is designed such that the sampling portion flows from the primary outlet at a rate no greater than a maximum air handling capacity of the mass-monitoring device.

* * * * *